(12) United States Patent
Scott

(10) Patent No.: US 10,661,055 B1
(45) Date of Patent: May 26, 2020

(54) CATHETER FOR LOCALIZED DRUG DELIVERY

(71) Applicant: Neal Scott, Mountain View, CA (US)

(72) Inventor: Neal Scott, Mountain View, CA (US)

(73) Assignee: Neal Scott, Mountain View, CA (US)

( * ) Notice: Subject to any disclaimer, the term of this patent is extended or adjusted under 35 U.S.C. 154(b) by 0 days.

(21) Appl. No.: 16/706,338

(22) Filed: Dec. 6, 2019

(51) Int. Cl.
*A61M 25/00* (2006.01)
*A61N 1/32* (2006.01)
*A61N 1/04* (2006.01)
*A61M 25/01* (2006.01)

(52) U.S. Cl.
CPC .... *A61M 25/0074* (2013.01); *A61M 25/0108* (2013.01); *A61N 1/0428* (2013.01); *A61N 1/325* (2013.01); *A61N 1/327* (2013.01); *A61M 2202/049* (2013.01); *A61M 2206/10* (2013.01)

(58) Field of Classification Search
CPC .......... A61M 25/0074; A61M 25/0108; A61M 2202/049; A61M 2206/10; A61M 25/1011; A61M 2025/1052; A61N 1/327; A61N 1/325; A61N 1/0428
See application file for complete search history.

(56) References Cited

U.S. PATENT DOCUMENTS

2011/0282274 A1* 11/2011 Fulton, III .......... A61M 1/3403
604/28

* cited by examiner

*Primary Examiner* — Lauren P Farrar
(74) *Attorney, Agent, or Firm* — Kim Rubin Patent Agent

(57) ABSTRACT

A device and method of treating proliferative disorders such as pancreatic cancer are described. Devices comprise an expandable mesh with two axial wings that seal against the inside of an enclosing blood vessel, creating an enclosed diffusion volume in the area subtended by the wings while permitting normal flow in the blood vessel through the ends of the mesh. A coaxial lumen provides for a guide wire, treatment drug tube, one or more flexible hypotubes and optionally electrical wires. The diffusion volume is set by the angle subtended by the wings causing the drug delivery to be radically directed toward a targeted tumor. Iontophoresis and electroporation electrodes on the mesh are used to directionally drive the drug through adjacent tissue and to temporarily increase the permeability of tissue through which the drug flows.

23 Claims, 3 Drawing Sheets

END VIEW AT CROSS-SECTION OF THE CATHETER

MESH WITH WINGS

END VIEW AT CROSS-SECTION OF THE CATHETER

CATHETER FOR LOCALIZED DRUG DELIVERY

BACKGROUND OF THE INVENTION

Prior art methods of treating proliferative disorders include systemic delivery of chemotherapy drugs. Dosage and frequency of these drugs is limited by their impact on healthy tissue and other side effects. Systemic delivery via the entire circulatory system of a patient delivers the drugs to all parts of the patient, rather than just a targeted tumor. For many proliferative disorders, chemotherapy concentration at the tumor is inadequate to completely eradicate the tumor. In disorders such as pancreatic cancer, prior art chemotherapy only extends life a few months. During these months, the quality of life of the patient is often low due to the chemotherapy side effects. Prior art includes a catheter with two inflatable balloons and with an infusion port between the balloons. As this device blocks blood flow, treatment time using the device is severely limited.

Prior art devices include drug infusion catheters that diffuse a drug radially in all directions from an infusion volume in the catheter. Such devices lack infusion directionality.

SUMMARY OF THE INVENTION

Embodiments of this invention overcome the above-cited weaknesses of prior art. Device and methods treat proliferative disorders such as pancreatic cancer.

A goal of devices and methods, and the problem to solve, is providing local, as compared to systemic, drug delivery to a patient. In addition to being local, drug delivery is radially directional.

In one embodiment, a medical device comprises a catheter with expandable regions at each end of a mesh. The expandable regions function like balloons in that they hold the mesh in place when expanded. However, unlike prior art inflatable balloons they do not block blood flow. The catheter includes a central lumen for a guide wire. The mesh is attached to two waterproof, flexible, axial "wings" that seal from the outside of the lumen to the interior sides of an enclosing blood vessel. The ends of the wings connect and seal at the expandable regions so that an isolated infusion volume is sealed from the flowing blood in the blood vessel. Blood flows normally in the blood vessel, through the mesh ends, around but not through the infusion volume. The pair of wings thus form two axial volumes around the core of the mesh: a sealed infusion volume and an open blood flow volume.

When the catheter is placed, the ends of the mesh are expanded, holding the mesh in place. A central portion of the mesh surface comprises a waterproof coating to isolate the infusion volume from the blood flow volume. The expandable mesh ends permit blood flow through the mesh. From an end view of the mesh, the flexible, waterproof wings extend outward from the central lumen to the walls of the enclosing blood vessel. They may not be symmetrically located. For example, they may subtend an angle of 120° for the infusion volume and thus 240° for the blood flow volume.

In use, the infusion volume comprises a treatment drug, such as a chemotherapy drug. This drug is typically delivered via a drug delivery tube extending through the catheter and then through a side port in the central portion of the mesh, into the infusion volume. The tube carries the treatment drugs, which typically come from a source outside the patient but may be from a source inside the patient.

In use, the treatment drug flows from the infusion volume, through the portion of the blood vessel side wall forming a surface of the infusion volume, into adjacent tissue. The mesh is placed and aligned so that the infusion volume is as close as possible to a tumor under treatment, with the infusion volume "facing" the tumor. The mesh is both aligned and rotated using the hypotubes. Unlike prior devices, when the mesh is placed and aligned, and the treatment drug is diffusing from the infusion volume through the wall of the enclosing blood vessel, blood continues to flow normally through the blood vessel, passing through the expanded mesh ends and through the blood flow volume parallel to the interior mesh lumen.

Features in some embodiments include electrodes on the device, ideally on the mesh, for iontophoresis, electroporation, or both, to drive a treatment drug towards and into the targeted tumor. One or more wires extend back from the electrodes, through the proximal end of the catheter to outside the patient.

Other aspects of the device are necessary for proper medical use of the catheter. A proximal and a distal flexible hypotube are used to expand the mesh. A guidewire is used to place the catheter.

Below is an abbreviated list of elements in one embodiment, identified with reference designators.

Figure 1:
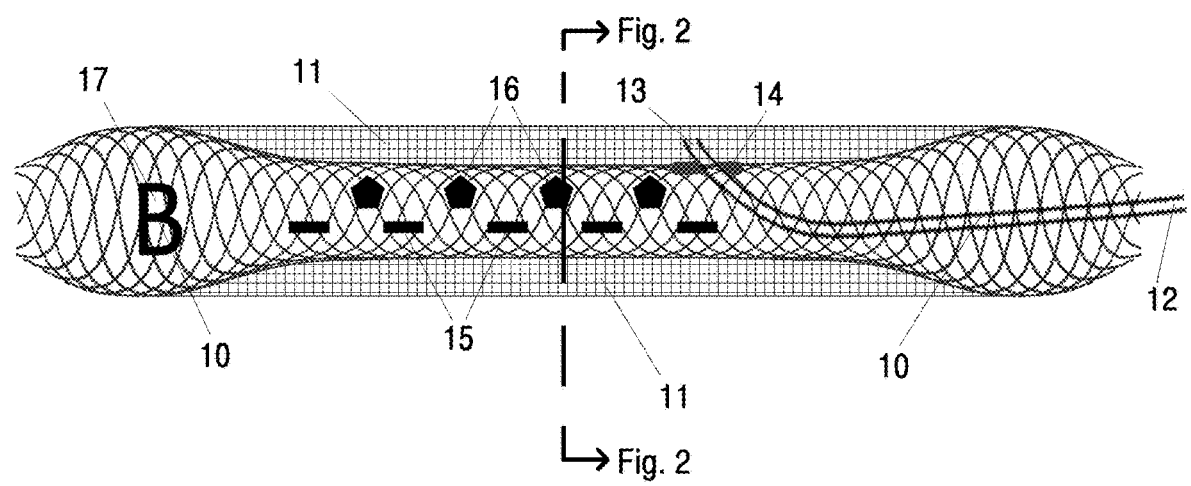
FIG. 1 shows a side view of a mesh with end expanded ends, wings and electrodes.
Figure 2:
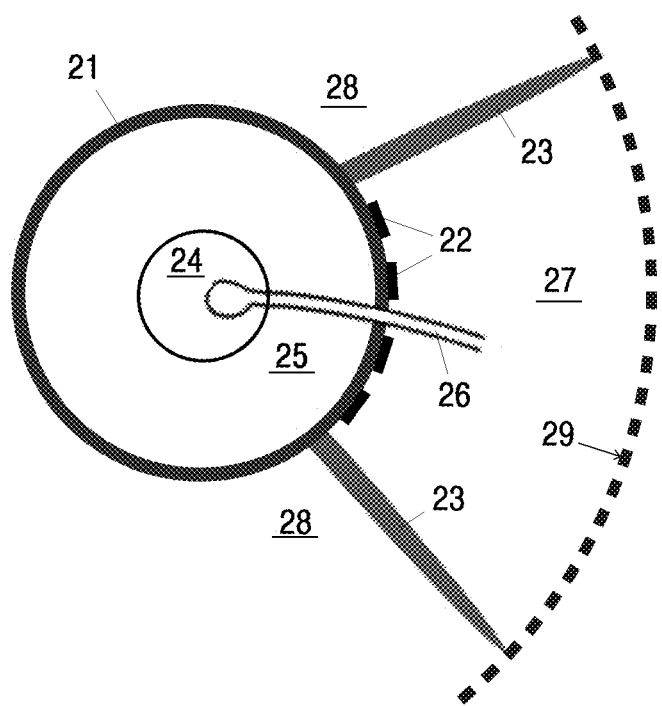
FIG. 2 shows an end view of a mesh with a central portion, balloons and wings.
Figure 3:
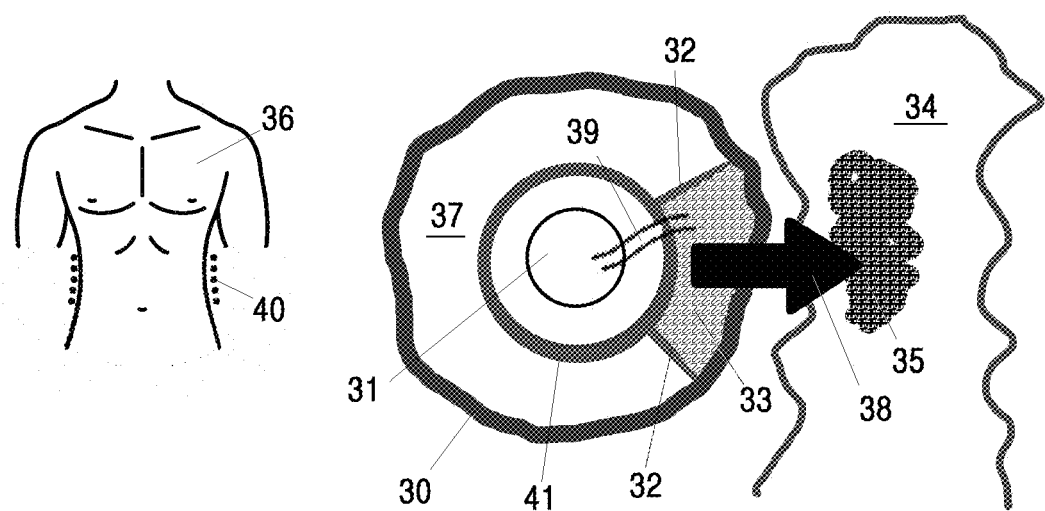
FIG. 3 shows placement of an embodiment in a patient.

FIG. 1
10 Side view of mesh with expanded balloons.
11 Wings.
12 Drug delivery tube extending from proximal end of a mesh.
13 End of drug delivery tube in infusion volume.
14 Port in sidewall of mesh for penetration of drug delivery tube.
15 Iontophoretic electrodes.
16 Electroporation electrodes.
17 Asymmetric radio-opaque marker.
FIG. 2
21 End view of mesh at cross-section
22 Electrodes
23 Wings.
24 Central lumen.
25 Interior of mesh.
26 Drug delivery tube.
27 Infusion volume.
28 Blood flow volume.
FIG. 3
30 End view of a blood vessel with a mesh installed.
31 Lumen portion of the mesh.
32 Two wings.
33 Infusion volume.
34 Organ with tumor.
35 Tumor under treatment.
36 Patient's torso.
37 Blood flow volume.
38 Direction of treatment drug flow.
39 Drug delivery tube.
40 Electrodes external to patient.
41 Mesh body.

DETAILED DESCRIPTION OF INVENTION

Embodiments, descriptions, scenarios and drawings are non-limiting. Descriptions below of a device and methods of use are exemplary scenarios.

Turning first to FIG. 1 we see a side view of a mesh portion of the catheter device with expanded and flared ends 10 and wings 11 at the sides. The mesh may be self-expanding or may be expanded by differential axial forces on a proximal and distal hypotube. The mesh may be constructed using a self-expanding stent. The wings are sufficiently flexible that they stretch when the mesh is contracted and expanded. When deployed, the outer edge of each wing presses against the interior of the enclosing blood vessel, not shown, creating the treatment volume and blood flow volume. A suitable blood vessel for some treatments includes the aorta. 12 shows a drug delivery tube exiting a central portion of the mesh, a lumen, not shown, into the infusion volume. Proximal, in this document, refers to the end of the mesh towards the direction from which the mesh is inserted. Note that proximal, in this context, is not the anatomical term used for body parts. 13 shows a port in the side of the mesh where the drug delivery tube penetrates from the lumen to the infusion volume. Embodiments may use multiple ports. The portion of the drug delivery tube upstream, proximal from the mesh, is not shown. The infusion volume and blood flow volume are not explicitly identified in this Figure. Coatings are not shown. Coatings may be or comprise a water-tight polymer. The blood vessels and surrounding tissue are not shown. This Figure is schematic only and should not be used to show relative sizes, materials, or other aspects of a mesh or other elements of the catheter device required for practical use. The distal end, or both ends, of the mesh may be tapered. Wings are critical for some embodiments as the creation of a drug infusion volume permits radially directional drug infusion towards a target, unlike prior art where drugs between two balloons in a blood vessel diffuse in all radial directions. The radial direction for drug infusion from the infusion volume is predetermined, dynamically adjustable, or both. The radial direction for drug infusion is typically towards a tumor or other proliferative disorder.

Some embodiments include electrodes on the mesh, or elsewhere on the device, for iontophoresis, electroporation, or both, to drive a treatment drug towards and into the targeted tumor. 15 shows schematically electrodes placed along the length of the mesh for electroporation. 16 shows schematically electrodes placed along the length of the mesh for iontophoresis. Shape, size and positions of electrodes may be quite different from those shown. Not shown are wires from the electrodes back through the blood vessel, to electronics. Such wires are typically, but not necessarily, through the lumen, a hypotube, or both. Such electronics may be located inside the patient, but more typically, outside the patient. When iontophoresis is used, additional electrodes on, in, or around the patient's body are required; these are not shown. Ideally, individual electrodes are driven independently. Either a cable with many wires may be used, or in another embodiment, the device includes demodulation electronics that takes a small number of conductors, or an optical cable as input, or wireless data as input, then outputs electronic signals to a larger number of individual electrodes. In iontophoresis, an electric field between the mesh and the target tumor drives electrically charged drug molecules, particles, ions, or carriers from the infusion volume towards the tumor. Charged biological drug carriers include liposome and micelles. Non-biological drug carriers include charged nanoparticles, for example, positively charged gold nanoparticles. Nanoparticles may be soluable. A treatment drug may be bound to a protein or an antibody. Treatment drugs may be bound to a radioactive atom or molecule. A treatment drug may be primarily a radioactive atom or molecule. Differential absorption of such a radioactive marker may be used to improve radiological imaging. The second set of electrodes may be wires or a grid surrounding the patient's torso, for example, see 40 in FIG. 3. Iontophoresis is a form of electrophoreses. Iontophoresis is a term preferred when transporting ions rather than individually charged particles.

In electroporation, current pulses are used to temporarily increase the permeability of the membranes of the nearby tissue and allow a treatment drug to enter target cells' plasma membranes more effectively. The iontophoresis electrodes are ideally controlled independently. Demodulation electronics in or proximal to the device may be used, similarly to iontophoresis electronics.

An asymmetrical radio-opaque marker, such as 17, may be placed on the mesh, such as at the distal end, to aid in precise and error-free positioning of the device. A similar marker may be placed on the patient's body to assist in alignment such as use of fluoroscopy. The letter, "B," as shown, is arbitrary for this Figure. Rotation of the mesh around its axis is accomplished typically by rotating one or more hypotubes. Any combination of elements (e.g. guide wire, two hypotubes, drug delivery tube, electric or electronic cabling, and optional imaging or monitoring elements) that extend from the mesh back to the proximal end of the enclosing blood vessel may be inside of one or more hypotubes, including a second hypotube.

A cross-section line is shown, marking a location for FIG. 2. The axis of the mesh is not shown explicitly; it is the obvious axis, parallel to the enclosing blood vessel, running horizontally in the Figure.

Turning now to FIG. 2 we see a schematic end view of a mesh at roughly the cross-section marked in FIG. 1. 21 shows a cross-section of the mesh body including a flexible, non-blood-permeable coating. The coating may be attached to an interior structure of the mesh; or attached to an exterior structure of the mesh; or may be incorporated in the matrix making up the structure of the mesh. The term coating as used herein, is not necessarily a "coating" as the word is commonly used; it may be an integral part of the mesh structure or a separate structure. 22 shows schematically electrodes for iontophoresis, electroporation or both, placed within the infusion volume created within the enclosing angle between the two wings 23. 24 shows an interior channel, the lumen, axial through the mesh, typically for a guide wire, not shown. 23 shows two wings. Typically one edge of the wings is attached to the mesh body 21 and optionally to a portion of the ends of the mesh. The opposing edges of the wings press against the interior walls 29 of the blood vessel. 26 shows a portion of a drug delivery tube. The infusion volume and the blood flow volume are not explicitly shown. An infusion volume 27 is between the wings. The blood flow volume would surround the remainder of the mesh 21, at the top, bottom and left of the Figure. The enclosing blood vessel is not shown. The end view of the body of the mesh is at a particular cross-section at or near the port, not shown. The port is the place in the mesh body 21 where the drug delivery tube 26 exits the lumen 25 into the infusion volume 27. The enclosing angle of the two wings that define the infusion volume is the range of 5° to 320°.

Another range is 25° to 220°. Another range is 45° to 180°. Another angle is 120°. Relative sizes and thicknesses of elements in this Figure are schematic only and typically not to scale. The infusion volume 27, in one embodiment, is defined by the two wings 23, a portion of the mesh 21, and an interior of the enclosing blood vessel. The portion of the mesh 21 that defines in part the infusion volume 27 may or may not include a portion of the ends of the mesh, 10 in FIG. 1. In some embodiments, the edge of the wings 23 where then connect to the mesh may be adjacent such that no portion or a small portion of the mesh is part of the perimeter of the infusion volume. Electrodes 22 are then on the mesh outside of the wings, or are on the wings.

Blood flow through the enclosing blood vessel while the catheter is functionally inserted is through remaining volume 28 (i.e., not the infusion volume 27) in the blood vessel. Some blood flow, ideally no blood flow is also through the lumen. Note that because FIG. 2 is a cross-section, the mesh diameter 21 is smaller than the blood vessel 29. Blood flow through the catheter when functionally deployed is through one expanded end of the mesh, 10 in FIG. 1, then around the sides of the mesh 21 in the central portion of the mesh 21, then out of the catheter through the other expanded end of the mesh. Such blood flow, in one embodiment, is thus through both the volume 28 and the volume 25, but not through the lumen 24. The percent of blood flow in the enclosing blood vessel that does not flow through the lumen 24 is in a range of 10% to 100%, 25% to 90%, 40% to 90%, greater than 50%, greater than 90%, greater than 95%, or 100%. In a preferred embodiment, the infusion volume 27 includes no ongoing blood flow in the enclosing blood vessel. However, some residual blood flow may pass through the infusion volume 27. This residual blood flow may be in the range of 0% to 50%, 0% to 15%, 0% to 5%, less than 10%, less than 2%, less than 0.5%, or 0%. Typically, any residual blood flow through the infusion volume is undesirable as it will both dilute the density of the treatment drug in the infusion volume and also cause some of the treatment drug to enter the patient's flowing blood.

Turning now to FIG. 3 we see an end view schematic of an embodiment in use. This cross-section is also at approximately the cross-section marking in FIG. 1; the expanded ends of the mesh, 10 in FIG. 1, are not shown. The body of the mesh is 41. The device shown in the Figure is deployed in a patient, often in the patient's torso 36, in a blood vessel 30. The central lumen is 31. Two wings are shown 32 with an edge of the wings against the interior of the blood vessel 30 and an opposing edge on the mesh 41. The blood flow volume is 37. 33 shows the infusion volume. 37 shows the blood flow volume. 39 shows a portion of the drug delivery tube extending from the central portion of the mesh into the infusion volume 33. An exemplary patient organ is shown 34. A targeted tumor is 35. The tumor 35 is treated, during use of an embodiment, by treatment drug flow from the drug delivery tube through ports in the lumen 31 and the mesh 41 into the infusion volume 33 and from there into the tumor tissue 35. This drug flow is shown by the large arrow 38. Ports in the lumen and the mesh wall are not shown explicitly; they are where the drug delivery tube 39 passes through the lumen and the mesh wall. The treatment drug delivery tube 39 typically comes from outside the patient 36, through the blood vessel 30 into the infusion volume 33. In some embodiments the treatment drug may come from inside the patient, such as from a reservoir, not shown. 40 shows one embodiment of a second set of electrodes for iontophoresis. The form of these electrodes may be a plate, wrapper, array, or grid of wires, terminals, needles, patches, or other conductors. Some embodiments or applications use needles penetrating at least a portion of the skin for better electrical conductivity through the patient. These may be multiple, small needles in a wrap or clothing worn by the patient. Alternatively or in addition, conductive patches on the skin may be used.

The ends of the flexible mesh 41 hold the mesh in place in the enclosing blood vessel 30. Blood flow in the blood vessel continues through the mesh ends, through the blood volume 37, but not through the lumen 31 or infusion volume 33, except in small quantities, in some embodiments. Note that a portion of the mesh that forms part of the infusion volume is impermeable to blood flow.

A method of use of the device includes the steps: (i) placing a catheter device embodiment into a patient blood vessel or other tubular structure; (ii) positioning axially and aligning rotationally the mesh proximal to and as close as possible to a treatment tumor; (iii) expanding the mesh; (iv) providing one or more treatment drugs, or other fluids, through a drug delivery tube into the infusion volume; (v) optional placement of external electrodes and powering electrodes for iontophoresis, electroporation or both; (vi) leaving the mesh in place for an effective time period.

In practice, additional medical steps are typically necessary, including treatment planning; patient preparation; imaging before, during and after mesh placement; patient monitoring; mesh removal; and repeat treatments as necessary.

An embodiment may be in a patient for highly variable time periods, such as from a minute, to hours or days, to permanent or semi-permanent placement. A treatment time may also vary considerably, from under a minute to hours or days. Repeat treatments may be used either with the same mesh or using a new mesh each treatment.

In an alternative embodiment a drug in the infusion volume 33 is not provided through treatment tube 39 but rather is part of or attached to the mesh 41 such that it is in the infusion volume 33 after placement. Typically, such a treatment drug would then slowly diffuse into the infusion volume 33 and thence into the tumor 35.

In yet another embodiment, electrodes for iontophoresis, electroporation, or both, are attached to or part of the mesh. See FIG. 2. Typically, the electrodes are attached to mesh body 41. However, they may be attached anywhere on the device embodiment, or may be separate structures proximal to the infusion volume.

In an embodiment, the medical device is shaped, sized, and configured for a particular type of location or treatment, or a particular type of tumor. Different devices may be selected by a medical practitioner as appropriate for a particular patient. The device may single use or may be for multiple uses.

In another embodiment, the medical device is adjustable so that a medical practitioner may adjust the shape, effective size, wing configuration, or other device attributes, dynamically, as appropriate for a particular patient.

In another embodiment, the medical device is custom manufactured or custom altered responsive to patient imaging and treatment desired by a medical practitioner. For example, all or part of a device may be 3D printed, based in part, on patient-specific imaging.

In another embodiment, the medical device is custom assembled by a medical practitioner, from a choice of device components or elements.

In another embodiment, the medical device is custom assembled by a medical practitioner, from a choice of device components or elements, responsive to patient-specific imaging and treatment desired by a medical practitioner.

Claimed method steps include patient-specific imaging as described elsewhere herein. Claimed method steps include patient-specific manufacturing or assembly, as described elsewhere herein.

Claimed treatment methods include the use of two or more treatment drugs used consecutively with the same device. Claimed treatment methods include the use of two or more treatment drugs used consecutively with different devices. One such additional treatment drug may be selected to improve the effect of a cytotoxic treatment drug on a tumor. One such additional treatment drug may be selected to minimize the effect of a cytotoxic drug on healthy tissue. One such additional treatment drug or chemical may be selected to improve patient imaging.

Three-Dimensional Imaging

Medical imaging has historically been primarily two-dimensional. For example, x-rays and sonograms images are planar. Positioning a medical device in an artery or vein is effectively one-dimensional: the distance of the device along the blood vessel. Software and other technologies exist to aggregate a series of two-dimensional image (or a series of one-dimensional data points, such as in Computer Aided Tomography) into a synthetic 3D electronic or software model.

Optimal use of device and method embodiments of this invention benefit from more expansive 3D modelling. The flow of drugs as they diffuse through a blood vessel wall towards a target tumor is inherently a three-dimensional problem. Various tissues are far from uniform. Each direction and path of drug flow will be different, depending the nature of tissue through which it is passing, voltages currents and waveforms at the electrodes, electric fields, the treatment drug(s), as well as other factors. As with all chemotherapy drugs, the goal is to put as much drug into tumor tissue and as little drug into healthy tissue as possible. In the prior art of systemic use of chemotherapy drugs, little or no 3D imaging was necessary. A selected dose and route, such as intravenously, is given to a patient and then the drug then moves throughout the patient's body without any additional, or minimal, medical guidance or control.

Using devices and methods of embodiments have more parameters available to the medical practitioner—or to software—to help design and manage treatment. As a few examples, both the distance along a blood vessel and circumferential orientation (rotation around the axis of the mesh) of the infusion volume must be carefully selected. Length of treatment is selectable, as well as drugs and drug concentrations. With the use of iontophoresis or electroporation, or both, vastly more variables are introduced, such as location of electrodes, voltages, current and time. Ideally, electrodes are controllable individually or in groups. Ideally, all adjustable parameters are set to maximize the fundamental goal: to put as much drug into tumor tissue and as little drug into healthy tissue as possible.

To this end, ideally, a first three-dimensional model is created of the patient's tissues, including the shape and nature of both the target tumor and nearby healthy tissue. That first model is then enhanced to a second model that includes optimal placement of the device. That second model is then enhanced to include selected drugs and concentration. Finally, the effects of various iontophoresis or electroporation are incorporated into the final model. These effects are highly variable as individual electrodes, their voltages, currents, waveforms and timing are adjustable. A doctor, medical technician or other medical practitioner, or medical software, observing and considering these models and variables, attempts to achieve the fundamental goal, including also the relative medical value of more aggressive tumor treatment with more healthy tissue damaged, or less damage to healthy tissue at the risk of less impact to the tumor. Additionally, the tumor itself may not be modeled a sharp-edged. It may be desirable, for example, to aggressively target a portion of the perimeter of the tumor to minimize metastasis or growth into specific adjacent organs. As another example, it may be desirable to reduce damage to a particularly critical nearby organ or structure. Thus, at least three different three-dimensional models are desirable. First, a static model of the tumor and surrounding tissue. Second, a flow model of how one or more treatment drugs move from the infusion volume through and into both tumor and healthy tissue. Third, a three-dimensional model of tissue damage. Note that for the second and third models, the model ideally includes changes with time. (A three-dimensional model that changes over time is sometimes called a four-dimensional model.) Embodiments explicitly include such three-dimensional models and their use in planning, executing and evaluating medical treatments and devices. Inputs to these models include known imaging, such as x-rays, sonograms, MRI, CAT scans, NMR imaging, PET imaging, angiography and fluoroscope images, as well as other imaging technologies. Such images are ideally both non-real-time and real-time. Ideally, during procedures, such 3D models are updated in real-time. Inputs to these models also include standard models for different types of tissue and infusion rates of different drugs under iontophoresis and electroporation. In one embodiment, finite element analysis (FEA) is used to drive these models. An iterative system, such as simulated annealing or Monte-Carlo analysis, may be used to set or recommend parameter settings. A simulator responsive to specific-patient attributes may be used to set or recommend parameter settings. Additional inputs and results monitoring may be used, such as biopsies, blood tests, and the like. Existing software, such as COMSOL Multiphysics, ANSYS, or Autodesk® Nastran® In-CAD may be used as a computational core or as an element in such modeling. Machine learning software may be used, once trained. A training set may be historical patient treatments and outcomes. A training set may be historical patient treatments and outcomes for patients treated with a device or method described herein.

Electrodes for iontophoresis create an electric field gradient. Therefore, electrodes are generally needed at both ends of a desired drug flow. One or both sets of electrodes are part of a device embodiments. There are multiple possible locations for the second set of electrodes. The electrodes may be surgically or percutaneously placed around the target tissue. They may be in the form of a grid or array around the patient's torso. They may be attached to the skin or penetrate the skin. They may be part of second invasive device placed in the patient. Individual electrodes may be very small. Thus, it is possible to use either a flexible or rigid needle comprising multiple electrodes as the second set of electrodes. Although invasive, use of a needle or hypotube to place electrodes has the potential to increase directionality and control of drug flow under iontophoresis.

Similarly, electrodes for electroporation are in or on a device embodiment. This may not be optimal placement, as the electrical pulses are likely to affect closest tissue more than distant tissue. Ideally, only tumor cells would be permeable to the chemotherapy drug. Thus, it may be advantageous to use a different or additional placement of electroporation electrodes. These electrodes may be in the form of needles, or multiple electrodes per needle, or placed by needles or hypotubes. Electrodes and wires leading to the electrodes benefit from good flexibility. One wire material with excellent flexibility is Cicoil Flexx-Sil™. Other finely stranded wire may be used. Suitable wire insulation materials include siloxanes, and PTFE.

Some embodiments comprise individual control of electrodes or groups of electrodes. Rather than running many wires from a device embodiment, through a tube to electronics outside the patient, an embodiment may comprise an electrical demodulator to permit a small number of wires, such as in the range of one to six, to control a large number of electrodes. Power for such a demodulator may come through such or similar wires. An alternative embodiment uses a local battery as an element of a device. If power is so supplied locally, input signals from outside the body may be via an optical cable or wirelessly, using radio signals that penetrate the body. In one embodiment, a device comprises a receiving antenna wire or wires for receiving such wireless input.

Some embodiments of use include "turning" an infusion path through tissue. For example, iontophoresis may be used to drive the infusion drug along a first path. Then, by energizing different iontophoresis electrodes, particularly external electrodes, the drug may then be driven along a different path or in a different infusion direction. This "turning" of a treatment drug during infusion is specifically claimed. Similarly, an infusion path may be "reversed." This may be used to drive a diffusing drug through a target region twice: once in the "outgoing" direction and then in an "inward direction." This also minimizes damage to healthy tissue on the far side of a tumor. Embodiments may use two or more treatment drugs in time sequence. For example, one drug may be used to help "prepare" tissue (either healthy or diseased), then followed by a cytotoxic treatment drug. As another example, use of a treatment drug such as a cytotoxic treatment drug may then be followed by a drug to help offset damage of the treatment drug, where this follow-up drug is driven only into healthy tissue, which may be closer to the infusion volume, or may be to a side of a tumor.

Yet another embodiment uses two different devices with different angular (angle subtended by the two wings) infusion volume, used sequentially for a single treatment. For example, a first cytotoxic drug may be used to target a larger diseased tissue volume, while a second cytotoxic drug or higher dose of the first drug is used to target the center or core of a tumor. Similarly, one drug may be use to target diseased tissue while a second drug is targeted at healthy tissue.

In some uses, it is desirable to have a treatment drug diffuse into a tumor for a relatively long period of time. An embodiment may be left in a patient for days, weeks, or semi-permanently. Rather than leave an invasive device penetrating the patient's skin for a long period, portions of the device, such as one or more hypotubes, or all skin penetrating elements, but not the infusion volume, may be removed. In some embodiments these may be re-attached later to continue treatment. In other embodiments, once the infusion volume is fully depleted, the mesh portion of an embodiment can then be also removed.

Yet another embodiment provides local delivery of anti-coagulants such as Heparin.

Yet another method of treatment embodiment treats difficult to manage cancers such as glioblastoma and sarcomas.

Yet another method of treatment embodiment treats organs that have been transplanted, or organs sensitive to an auto-immune disease or auto-immune response. For example, immunosuppressant drugs may be diffused into a transplanted organ to reduce immune response that might cause that organ to degrade or be rejected. Example immunosuppressant drugs include: calcineurin inhibitors, antiproliferative agents, mTOR inhibitors, and steroids. Examples of organs that may be treated include kidneys, hearts and lungs. Such methods may be used to treat autoimmune diseases by treating specific organs or areas of a patient body that are most affected or most critical to the patient. Such organs include connective tissue and endocrine glands such as the thyroid or pancreas.

Yet another method of treatment embodiment causes an abortion, where the womb is targeted tissue for treatment.

Yet another method of treatment embodiment uses hormones as a treatment drug. Targeted tissue includes organs or tissue that are particularly responsive to hormones. Targeted tissue includes organs or tissue that are particularly sensitive a lack of a hormones. For example, a vagina may be the treatment vessel and vaginal atrophy, or other disorders of the female reproductive system, such as cramps or painful periods, may be a condition being treated. Examples of hormones for such treatments include estrogen, progesterone, androgens, leuprolide acetate, and steroids or other anti-inflammatory drugs.

Yet another method of treatment embodiment treats diseases or conditions of the stomach or other organs of the digestive system. For example, stomach tumors or ulcers may be treated using either a blood vessel or the stomach or other portions of the alimentary system as the enclosing vessel. Treatment drugs may include cytotoxic drugs, anti-inflammatory drugs, proton pump inhibitors, or anti-viral drugs. Another embodiment treats irritable bowel disease, where the enclosing vessel is part of the alimentary canal. An entry point for the device may be the mouth or anus. Another method of treatment is for irritable bowel syndrome (IBS). Treatment drugs include anti-inflammatory drugs, antibiotics, anti-viral drugs, hormones and muscle relaxants. Treatment drugs may include microflora.

Yet another method of treatment embodiment treats areas of acute infection or potential infection. A treatment drug may be an antibiotic or analgesic drug.

Yet another embodiment includes treatment of joints. Joints may be affected by arthritis, for example. Anti-inflammatory drugs may be used for such treatment. A joint capsule may the treatment location of a device. A joint capsule may the targeted tissue.

Suitable Materials

Suitable materials for a mesh include stainless steel, Elgiloy, cobalt chromium, Nitinol and tantalum.

Suitable materials for hypotubes include stainless steel, cobalt chromium, Elgiloy, Nitinol, Tantalum, polymer, and metal-polymer combinations.

Suitable materials for a flexible, expandable coating on the mesh or wings include expandable polymers, siloxanes, ethylene vinyl acetate and hydrogel.

Suitable materials for electrodes include stainless steel, cobalt chromium, copper containing alloys, silver containing alloys, lead containing alloys, gold and gold containing alloys, Ag—AgCl, and conductive polymers. Electrodes may comprise a paste or gel. A suitable current is 4 mA/cm2, or in the range of 0.1 to 100 ma/cm2. However, ideal currents and waveforms are highly case specific. For the external electrodes for iontophoresis conductive skin patches may be used.

Suitable anti-proliferative drugs, particularly for pancreatic cancer, include gemcitabine and a combination containing oxaliplatin, irinotecan, leucovorin and fluorouracil (called Folfirinox). Other drugs for other types of cancers or proliferative disorders may be different. Suitable placement of a device for treatment of pancreatic cancer is in the aorta or vena cava, with the infusion volume directed towards the pancreas or towards a portion of the tumor that has spread.

Local and directional drug delivery with a device may be enhanced with drugs that improve venous permeability such as histamine, bradykinin, and the like. Such drugs may be combined the treatment drugs or may be administered systemically, such as intravenously or orally.

Suitable material for a mesh is a self-expanding metal stent. A mesh may be expanded in the usual way using a pair of flexible hypotubes. In the portion of mesh that is part of an infusion volume is coated with a flexible, expandable, water-impermeable coating or material incorporated into the mesh matrix, such as a polymer. Expanding the mesh deploys the wings against the interior sides of the enclosing blood vessel, if not already so deployed. Note that the ends of the mesh are not necessarily coated with a waterproof coating as they pass blood in the enclosing blood vessel.

Although in this document an anatomical "blood vessel" is used extensively, this term should be construed to include to other tubular structures within a patient, such as the bile duct, cystic duct, pancreatic duct, trachea, a bronchus, urethra, vagina, or portions of the alimentary canal. Blood vessels include veins and arteries. Another name for the device is a catheter. For non-blood-vessel devices and application, the ends of the mesh may be non-permeable, as flow in such a non-blood tubular structure may be non-critical or less critical. That is, in some embodiments, the entire mesh is or is coated with a non-permeable coating.

Although we refer in this document to "tumors" this term should be construed to include any proliferation disorder. Additionally, the devices and methods of embodiments include treatment for non-proliferation disorders, any tissue, healthy or unhealthy, desirous or undesirous, if it responds to a drug, it may be a candidate for use of the described devices and methods for treatment. Embodiments for methods of treatment include reduction or removal of undesirable, but otherwise healthy, tissue, such as fat or scar tissue, or to improve cosmetic appearance of the patient. Some embodiments use an artificially constructed body cavity or tubular structure. For example, next to fat, scar tissue or under the skin. In this context, "tumor" includes any undesirable tissue.

We may refer to an embodiment of a medical device as a catheter. The medical term, "catheter" is not formally defined in the art; therefore we sometimes use the term, "medical device." The term, "catheter," is used for readability and is not limiting. In some contexts the entire device may be called a mesh. Some embodiments include elements outside of the mesh in the medical device such as the conductors 40 shown in FIG. 3. Embodiments are not limited by terminology such as catheter and mesh. All embodiments of devices comprise multiple elements, include a "standalone" mesh and a tube through which control hypotubes, a drug delivery tube, and electrical (or optical or wireless) wiring may be routed. Correct construction of these terms is context sensitive.

While we generally refer to an "infusion volume," an alternative name is "diffusion volume." A treatment drug is "diffused from" the infusion volume into adjacent tissue. The treatment drug is "infused into" adjacent tissue and a targeted tumor or other targeted tissue.

We refer to chemotherapy drugs herein. Chemotherapy drugs should be construed for some embodiments (but not all embodiments) to also include treatment drugs for other types of proliferative disorders and disorders that are not proliferative. For example, embodiments for local delivery of treatments for kidney and liver disorders are also claimed. Systemic chemotherapy drugs sometime damage healthy organs as a side effect, including heart, lungs, liver, kidneys, bladder, muscles, skin, and male and female reproductive systems. Claimed embodiments include local delivery of treatment drugs for these organs in response to chemotherapy side effects. Claimed embodiments also include local drug delivery to treat body parts affected by autoimmune diseases. A list of autoimmune diseases may be found at: https://www.aarda.org/diseaselist. Embodiments include treatment drugs for Rheumatoid arthritis, Hashimoto's autoimmune thyroiditis, Celiac disease, Graves' disease, Diabetes mellitus, type 1, Vitiligo, Rheumatic fever, and Pernicious anemia/atrophic gastritis. Drugs used to treat autoimmune disorders include anti-inflammatory agents such as prednisone, methylprednisolone, and dexamethasone. Other drugs that suppress the immune system but are not corticosteroids include sirolimus, methotrexate, and cyclophosphamide. Another group of drugs include biologic response modifiers, and disease-modifying drugs, including etanercept, belimumab, and infliximab. Yet another embodiment includes local delivery of an antithrombin that inhibits platelet-dependent thrombosis, such as, hirulog, heparin, abciximab, eptifibatide, and Phe-pro-arg chloromethyl ketone. Other anticoagulants include apixiban, revoroxaban, warfarin, or similar agents. For diseases and cases where local delivery of a drug is not possible, the best available treatment using embodiments may be minimizing side effects. Yet another embodiment uses as a treatment a drug such as paclitaxel that is loaded into charged liposomes.

The term "treatment drug" includes a plurality of treatment drugs and includes ancillary drugs or compounds that improve the flow, diffusion, infusion retention, electrical charge, effectiveness, safety, stability, or detectability of a treatment drug. Treatment drugs may be enclosed, packaged or bonded with biological elements, such as liposomes. Treatment drugs may be enclosed, packaged or bonded with non-biological elements such as biodegradable nanoballs. Treatment drugs may be enclosed, packaged or bonded with a charged or ionic compound to aid in iontophoresis or electrophoreses.

Yet another embodiment provides local and directional delivery of drugs in an artery upstream from a target organ or body part, or a nearby vein. Although drugs delivered in this mode have poor retention, embodiments permit long-term placement of devices and thus may counteract or mitigate the otherwise poor retention. Embodiments include such long-term placement of devices and methods of treatment, even when traditional retention is poor. Placement of devices may be in the range of 2 to 60 minutes, 10 minutes to two hours, one hour to eight hours, one hour to 72 hours, and longer than one hour.

Embodiments include devices that are custom designed for a patient. Typically, the design of such custom designed devices is responsive to the 3D modelling described above. Other embodiments use a unique design for each location of a tumor or a particular blood vessel to be used.

In one embodiment, the device does not include wings but does include electrodes for both iontophoresis and electroporation where electrodes may be controlled individually or in groups. The device is secured by expanding the mesh at a desired location within a blood vessel or other patient tubular structure.

Method claims that refer to a device claim are construed where the reference to the embedded device claim may be replaced by exactly the elements and other limitations in the device claim. Device claims that refer to a method claim are construed where the embedded method claim may be replaced by exactly the steps and other limitations of the method claim.

Ideal, Ideally, Optimal and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification and drawings. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substation thereof to any and all other device claims, including all combinations of elements in device claims. Claims for devices and systems may be restricted to perform only the methods of embodiments or claims.

I claim:

1. A medical device for local delivery of a treatment drug to a patient comprising:
   an expandable mesh, comprising:
      a mesh material;
      a primary mesh axis;
      an internal volume; and
      comprising two mesh flared ends;
   two or more blood-impermeable wings between the two mesh flared ends, coaxial with the mesh axis, outside of the mesh internal volume; comprising a first edge attached to the mesh and comprising a second, opposing edge adapted to seal against an interior wall of a tubular structure of the patient; adapted so that when the medical device is placed in the tubular structure and the mesh is expanded, an infusion volume in the tubular structure is created, isolated from the remainder of the tubular structure, wherein the infusion volume periphery is defined by the two wings and a portion of the interior wall of the tubular structure, and optionally further defined by a portion of the mesh;
   an infusion port located between an interior of the mesh and the infusion volume.

2. The medical device of claim 1 further comprising:
   one or more exposed iontophoresis electrical conductors adapted to function as one electrode for iontophoresis.

3. The medical device of claim 1 further comprising:
   one or more exposed electroporation electrical conductors.

4. The medical device of claim 1 further comprising:
   an asymmetric radiographic marker.

5. The medical device of claim 1 further comprising:
   one or more hypotubes.

6. The medical device of claim 1 further comprising:
   a non-blood-permeable coating on the mesh.

7. The medical device of claim 1 wherein:
   the tubular structure in the patient is a blood vessel.

8. The medical device of claim 7 wherein: a mesh is adapted to permit blood flow through the mesh when the device is placed in a blood vessel of the patient.

9. A method of medical treatment of proliferative disorders comprising the steps:
   placing the device of claim 1 in the patient proximal to a target tissue;
   expanding the mesh;
   providing the treatment drug into the infusion volume.

10. The method of medical treatment of claim 9 comprising the additional steps:
    powering the one or more exposed first electrical conductors to enable iontophoresis;
    performing iontophoresis to move the treatment drug from the infusion volume to the target tissue.

11. The method of medical treatment of claim 9 wherein:
    the tumor is in the patient's pancreas; and
    wherein the proximal location of the device is in the patient's aorta or vena cava.

12. The method of medical treatment of claim 9 wherein:
    the treatment drug is an antiproliferation drug.

13. The method of medical treatment of claim 9 wherein:
    the tumor is inoperable prior to treatment of claim 9.

14. The method of medical treatment of claim 9 wherein:
    the tumor is a neuroblastoma or sarcoma.

15. The method of medical treatment of claim 9 wherein:
    the drug is cytotoxic.

16. The method of medical treatment of claim 9 wherein:
    the drug is chemotherapeutic.

17. The method of medical treatment of claim 9 comprising the additional step:
    orienting the device so that the infusion volume is oriented towards the target tissue.

18. The method of medical treatment of claim 9 comprising the additional step:
    placing one or more additional iontophoresis electrodes on or external to the patient's skin such that the iontophoresis conductors and the one or more additional iontophoresis electrodes create an electrical field gradient.

19. The method of medical treatment of claim 9 wherein:
    the device further comprises one or more exposed electroporation electrical conductors adapted to function for electroporation;
    powering the one or more exposed second electrical conductors with an appropriate voltage or current and waveform to cause effective electroporation.

20. The method of medical treatment of claim 9 comprising the additional step:
    placing the device in the patent for a continuous period of four hours or longer.

21. The method of medical treatment of claim 9 comprising the additional step:
 placing at one or more external electrodes, comprising at least a portion of a cylinder, around a trunk or limb of the patient;
 performing electroporation using the one or more electroporation electrical conductors and the one or more external electrodes.

22. The method of medical treatment of claim 9 comprising the additional step of:
 performing both iontophoretic and electroporation using the device in the patient.

23. The method of medical treatment of claim 9 comprising the additional steps:
 using software for modeling three-dimensional flow of the treatment drug from the device into the patient, wherein the model is responsive to the medical status and needs of the patient, location and extent of the target tissue in the patient, one or more selected treatment drugs; treatment time; and
 placing the device in the patient.

\* \* \* \* \*